(12) United States Patent
Sawada et al.

(10) Patent No.: US 12,417,619 B2
(45) Date of Patent: Sep. 16, 2025

(54) IMAGE ANALYZING DEVICE

(71) Applicant: SHIMADZU CORPORATION, Kyoto (JP)

(72) Inventors: Ryuji Sawada, Kyoto (JP); Shuhei Yamamoto, Kyoto (JP); Takeshi Ono, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 366 days.

(21) Appl. No.: 18/027,799

(22) PCT Filed: Apr. 27, 2021

(86) PCT No.: PCT/JP2021/016739
§ 371 (c)(1),
(2) Date: Mar. 22, 2023

(87) PCT Pub. No.: WO2022/070491
PCT Pub. Date: Apr. 7, 2022

(65) Prior Publication Data
US 2023/0334832 A1    Oct. 19, 2023

(30) Foreign Application Priority Data
Sep. 29, 2020  (JP) ................ 2020-163306

(51) Int. Cl.
*G06V 10/774* (2022.01)
*G06T 7/00* (2017.01)
(Continued)

(52) U.S. Cl.
CPC .......... *G06V 10/774* (2022.01); *G06T 7/0012* (2013.01); *G06V 10/776* (2022.01);
(Continued)

(58) Field of Classification Search
None
See application file for complete search history.

(56) References Cited

U.S. PATENT DOCUMENTS

| 12,045,934 B2 * | 7/2024 | Bigos ................ G06V 10/7747 |
| 2019/0156474 A1 * | 5/2019 | Watanabe ............ G06T 7/001 |

(Continued)

FOREIGN PATENT DOCUMENTS

| JP | 8-44851 A | 2/1996 |
| JP | 2018-116376 A | 7/2018 |

(Continued)

OTHER PUBLICATIONS

Communication dated Sep. 5, 2023, issued in Japanese Application No. 2022-553451.

(Continued)

*Primary Examiner* — Tsung Yin Tsai
(74) *Attorney, Agent, or Firm* — Sughrue Mion, PLLC (57) ABSTRACT

An image analyzing device (1) includes an image holder (8) that holds an image, a trained model registration part (10) configured to register trained models created by machine learning, a trained model holder (12) that holds the trained models registered by the trained model registration part (10), an algorithm holder (14) that holds a plurality of analysis algorithms for executing analysis processing of an image, a recipe creation part (18) configured, for an image to be analyzed optionally selected from among images held in the image holder (8), to create an analysis recipe for analyzing the image to be analyzed by combining a trained model selected from the trained models held in the trained model holder (10) and an analysis algorithm optionally selected from the plurality of analysis algorithms held in the algorithm holder (14), and an analysis execution part (20) configured to execute analysis of the image to be analyzed based on the analysis recipe created by the recipe creation part (18).

11 Claims, 7 Drawing Sheets

(51) Int. Cl.
*G06V 10/70* (2022.01)
*G06V 10/776* (2022.01)
*G06V 20/69* (2022.01)

(52) U.S. Cl.
CPC .............. *G06V 10/87* (2022.01); *G06V 20/69* (2022.01); *G06T 2207/10056* (2013.01); *G06T 2207/10064* (2013.01); *G06T 2207/20081* (2013.01); *G06T 2207/30024* (2013.01); *G06T 2207/30072* (2013.01)

(56) References Cited

U.S. PATENT DOCUMENTS

| | | | |
|---|---|---|---|
| 2020/0042825 A1* | 2/2020 | Nguyen | G06F 18/285 |
| 2020/0167601 A1* | 5/2020 | Deng | G06T 7/269 |
| 2022/0309745 A1* | 9/2022 | Bigos | G06V 10/7747 |

FOREIGN PATENT DOCUMENTS

| | | |
|---|---|---|
| WO | 2019/003355 A1 | 1/2019 |
| WO | 2020/188814 A1 | 9/2020 |

OTHER PUBLICATIONS

Japanese Office Action dated Jan. 30, 2024 in Application No. 2022-553451.
Aoki et al., "ACTIT: Automatic Construction of Tree-structural Image Transformations", ACTIT, 1999, pp. 888-894, vol. 53, No. 6.
Written Opinion for PCT/JP2021/016739 dated Jun. 15, 2021.
International Search Report for PCT/JP2021/016739 dated Jun. 15, 2021.
Communication issued Jun. 17, 2025 in Japanese Application No. 2024-086153.
Communication issued Jun. 27, 2025 in Chinese Application No. 202180061616.8.

* cited by examiner

| Culture condition | To be analyzed | For training 1 | For training 2 | Use |
|---|---|---|---|---|
| — — — | | | | Training Evaluation Test |
| — — — | | | | Training Evaluation Test |
| — — — | | | | Training Evaluation Test |
| — — — | | | | Training Evaluation Test |
| — — — | | | | Training Evaluation Test |
| — — — | | | | Training Evaluation Test |
| | | | | |

IMAGE ANALYZING DEVICE

This Application is a National Stage of International Application No. PCT/JP2021/016739 filed Apr. 27, 2021, claiming priority based on Japanese Patent Application No. 2020-163306 filed Sep. 29, 2020.

TECHNICAL FIELD

The present invention relates to an image analyzing device.

BACKGROUND ART

In analysis using image processing, estimation processing of estimating a region and a position of an object to be analyzed, such as a cell and a nucleus of the cell, which are shifted to an image to be analyzed is performed, but this estimation processing requires a parameter for distinguishing between the object to be analyzed and a portion other than the object to be analyzed, and setting of such a parameter is not easy and has been time-consuming work.

In recent years, image analysis using machine learning has been proposed and implemented (see Patent Document 1). In image analysis using machine learning, a computer is caused to compare an image to be analyzed with a label image (an image indicating a boundary or the like of an object to be analyzed in the image to be analyzed), so that the computer automatically acquires a parameter or the like necessary for identifying a region of the object to be analyzed or a position of a specific portion in the image to be analyzed. Then, by causing the computer to remember an acquisition result as a trained model and applying the trained model to another image to be analyzed, it is possible to cause the computer to automatically estimate a region or a specific position of an object to be analyzed in the image to be analyzed.

PRIOR ART DOCUMENT

Patent Document

Patent Document 1: Japanese Patent Laid-open Publication No. 2019-148950

SUMMARY OF THE INVENTION

Problems to be Solved by the Invention

What kind of analysis is performed on an image to be analyzed varies depending on the user. However, in an existing image analyzing device, there has been a problem that it is not easy to newly create a trained model suitable for an image to be analyzed or freely combine desired analysis processing with a created new trained model, and a work load of the user is large.

In view of the above, an object of the present invention is to reduce a work load of the user in image analysis using machine learning.

Solutions to the Problems

A first embodiment of an image analyzing device according to the present invention includes an image holder that holds an image, a trained model registration part configured to register trained models created by machine learning, a trained model holder that holds the trained models registered by the trained model registration part, an algorithm holder that holds a plurality of analysis algorithms for executing analysis processing of an image, a recipe creation part configured, for an image to be analyzed optionally selected from among images held in the image holder, to create an analysis recipe for analyzing the image to be analyzed by combining a trained model selected from the trained models held in the trained model holder and an analysis algorithm optionally selected from the plurality of analysis algorithms held in the algorithm holder, and an analysis execution part configured to execute analysis of the image to be analyzed based on the analysis recipe created by the recipe creation part.

Here, the "analysis recipe" means a set of a plurality of algorithms necessary for executing desired analysis on an image to be analyzed.

A second embodiment of the image analyzing device according to the present invention includes an image holder that holds a plurality of images obtained by imaging each of a plurality of cell culture wells provided in a cell culture plate in a state of being associated with a culture condition of a cell in the imaged cell culture well, a recipe creation part configured to select a plurality of images for training corresponding to a plurality of images to be analyzed optionally selected from among images held in the image holder, to create a plurality of data sets for training by combining, based on the culture condition associated with each image, the image to be analyzed and the image for training corresponding to each other, and to create an analysis recipe for creating a trained model for image analysis by performing machine learning using the plurality of data sets for training, and an analysis execution part configured to create the trained model based on an analysis recipe created by the recipe creation part.

Effects of the Invention

According to the first embodiment of the image analyzing device according to the present invention, not only an existing trained model but also a new trained model can be held in the trained model holder, and an analysis recipe can be created by combining a trained model held in the trained model with an optional analysis algorithm held in the algorithm holder with respect to an image to be analyzed, so that an analysis recipe necessary for executing analysis processing desired by the user can be easily created. By the above, a work load of the user in image analysis using machine learning is reduced.

According to the second embodiment of the image analyzing device according to the present invention, an image for training corresponding to each of a plurality of images to be analyzed is automatically selected based on a culture condition associated with an image, and a data set for training for machine learning is created. Therefore, a workload of the user related to creation of a trained model is reduced.

EMBODIMENTS OF THE INVENTION

Hereinafter, an example of an image analyzing device according to the present invention will be described with reference to the drawings.

Figure 1:
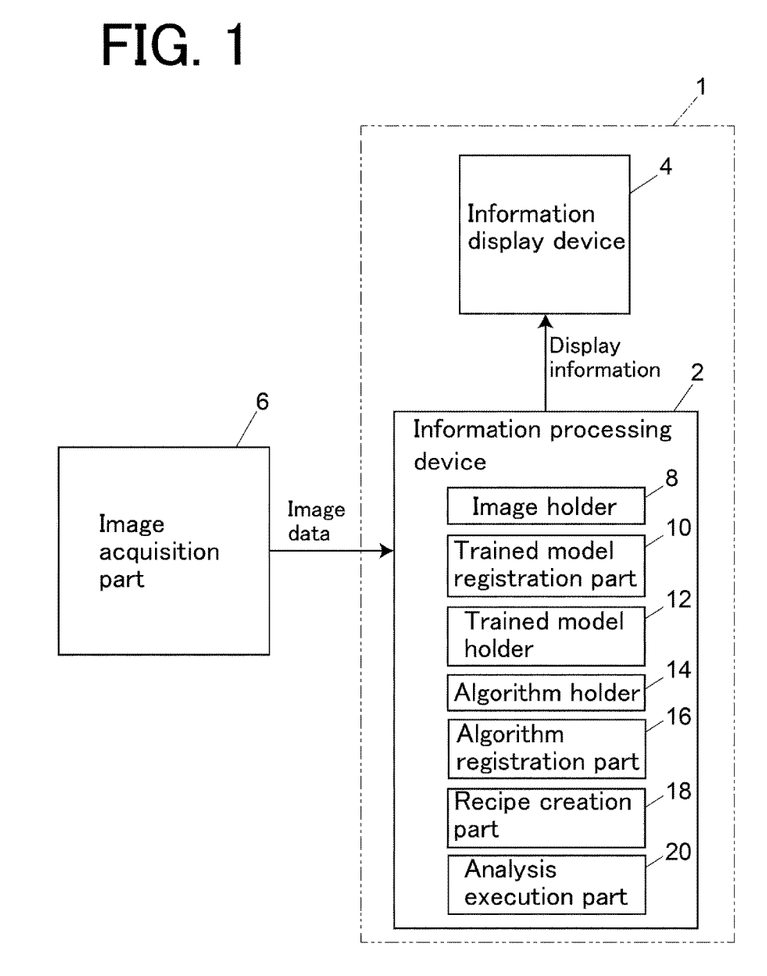
FIG. 1 is a block diagram illustrating an example of an image analyzing device.

FIG. 1 illustrates a schematic configuration of an image analyzing device 1.

The image analyzing device 1 includes an information processing device 2 and an information display device 4. The information processing device 2 has a function of taking in image data acquired by an image acquisition part 6 and performing analysis processing. The information processing device 2 is a computer device (for example, a personal computer) including an information storage medium such as a hard disk drive and an electronic circuit including a central processing part (CPU), in which a computer program for realizing each function to be described later is introduced. The information display device 4 is a display (for example, a liquid crystal display) communicably connected to the information processing device 2. Examples of the image acquisition part 6 include a microscope (for example, a phase contrast microscope or a fluorescence microscope) for imaging the inside of each well of a cell culture plate.

The information processing device 2 includes an image holder 8, a trained model registration part 10, a trained model holder 12, an algorithm holder 14, an algorithm registration part 16, a recipe creation part 18, and an analysis execution part 20. The trained model registration part 10, the algorithm registration part 16, the recipe creation part 18, and the analysis execution part 20 are functions realized by the CPU executing a predetermined computer program introduced in the information processing device 2. The image holder 8, the trained model holder 12, and the algorithm holder 14 are functions realized by a partial storage area of an information storage medium in the information processing device 2.

The image holder 8 holds an image obtained by imaging each of a plurality of cell culture wells provided in a cell culture plate with a phase contrast microscope, an image obtained by fluorescently staining a cell and a nucleus in the same cell culture well and imaging the cell and nucleus with a fluorescence microscope, a label image obtained by processing a fluorescence microscope image, and the like in a state associated with a culture condition of a cell in each cell culture well. Association between an image and a culture condition can be realized, for example, by attaching a culture condition to a file name of image data according to a predetermined rule.

The trained model registration part 10 is configured to register a new trained model necessary for image analysis. The trained model is information such as a parameter necessary for image analysis acquired by machine learning executed using a certain image and a label image of the image. By applying the trained model to another image to be analyzed, it is possible to estimate a cell region shown in the image to be analyzed, and it is possible to perform analysis such as obtaining an area of the cell region in the image using the estimation result and counting the number of cell nuclei. The trained model registered by the trained model registration part 10 may be one created by the image analyzing device 1 or one created by another image analyzing device. The trained model registered by the trained model 10 is held in the trained model holder 12.

The algorithm holder 14 holds a plurality of types of analysis algorithms necessary for executing image analysis. Analysis algorithms held in the algorithm holder 14 include not only an algorithm for executing analysis processing such as estimation of a cell region in an image to be analyzed using a trained model, calculation of an area of a cell region in an image, and counting of the number of cells, but also an algorithm for executing training processing of creating a trained model using an image to be analyzed and a label image. That is, the image analyzing device 1 has a function of creating a new trained model using an image to be analyzed and a label image and executing desired analysis processing using the trained model even if there is no existing trained model.

The algorithm registration part 16 is configured to register a new analysis algorithm. The analysis algorithm registered by the algorithm registration part 16 is held in the algorithm holder 14.

The recipe creation part 18 is configured to create an analysis recipe necessary for executing analysis processing desired by the user on an image to be analyzed. In creating the analysis recipe, the user can optionally select a trained model to be applied to an image to be analyzed and an algorithm of analysis processing to be executed, and the recipe creation part 18 combines the trained model and the analysis algorithm selected by the user to create an analysis recipe of analysis processing on the image to be analyzed.

The analysis execution part 20 is configured to execute analysis processing on an image to be analyzed based on the analysis recipe created by the recipe creation part 18.

Figure 2:
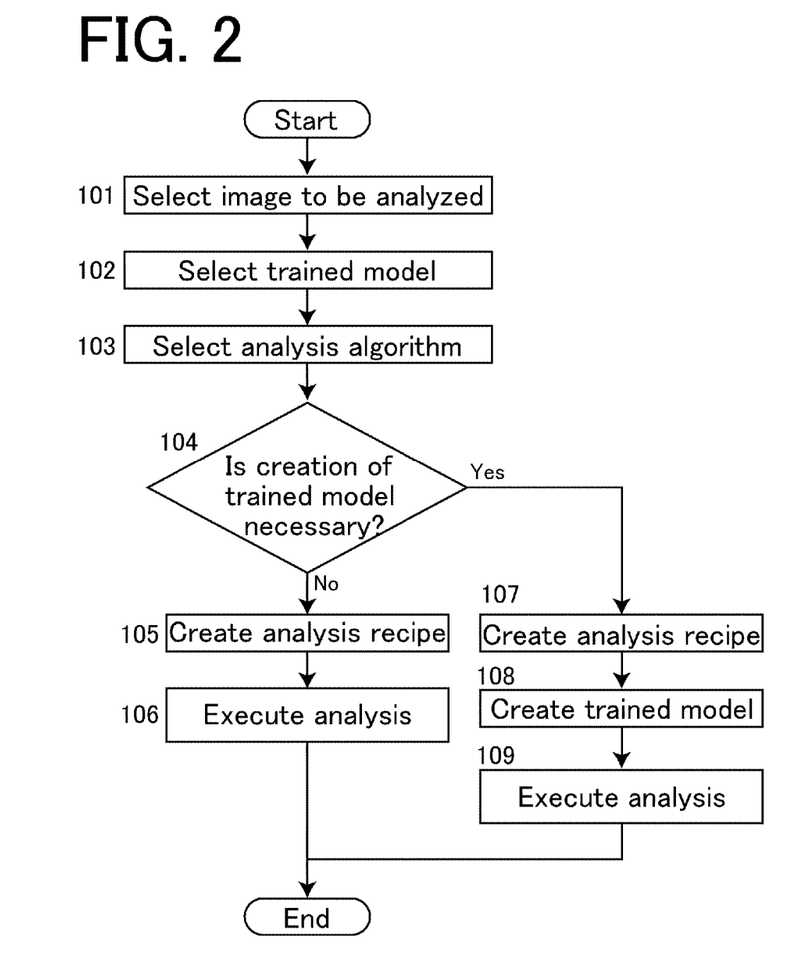
FIG. 2 is a flowchart schematically illustrating an example of operation up to image analysis in the example.

A series of processes until the analysis processing is executed on an image to be analyzed will be described with reference to a flowchart of FIG. 2.

The recipe creation part 18 displays an input screen for selecting an image to be analyzed, a trained model, and an analysis algorithm on the information display device 4, and on the screen, the user performs selection of an image to be analyzed (Step 101), selection of a trained model (Step 102), and selection of an analysis algorithm (103). Note that, in selecting a trained model, in a case where there is no existing trained model, in a case where there is no trained model to be applied to an image to be analyzed, in a case where image analysis that does not require estimation processing by application of a trained model is desired, or the like, the user can select no trained model. Further, when selecting an analysis algorithm, the user can select a plurality of analysis algorithms.

The recipe creation part 18 determines whether or not it is necessary to create a new trained model based on input information from the user in steps 101 to 103 (Step 104), and, if it is not necessary to create a new trained model, creates an analysis recipe including estimation processing using the selected trained model or an analysis recipe not using a trained model (in a case where no trained model is selected) (Step 105). The analysis execution part 20 executes analysis processing using the selected analysis algorithm according to the analysis recipe created by the analysis recipe creation part 18 (Step 106).

Further, in a case where it is determined to be necessary to create a new trained model (Step 104: Yes), the recipe creation part 18 creates an analysis recipe including machine learning after creating a data set for training necessary for creating a trained model and the like (Step 107). The analysis execution part 20 creates a trained model according to the analysis recipe created by the analysis recipe creation part 18 (Step 108), and executes analysis processing using the created trained model and the selected analysis algorithm (Step 109).

Figure 3:
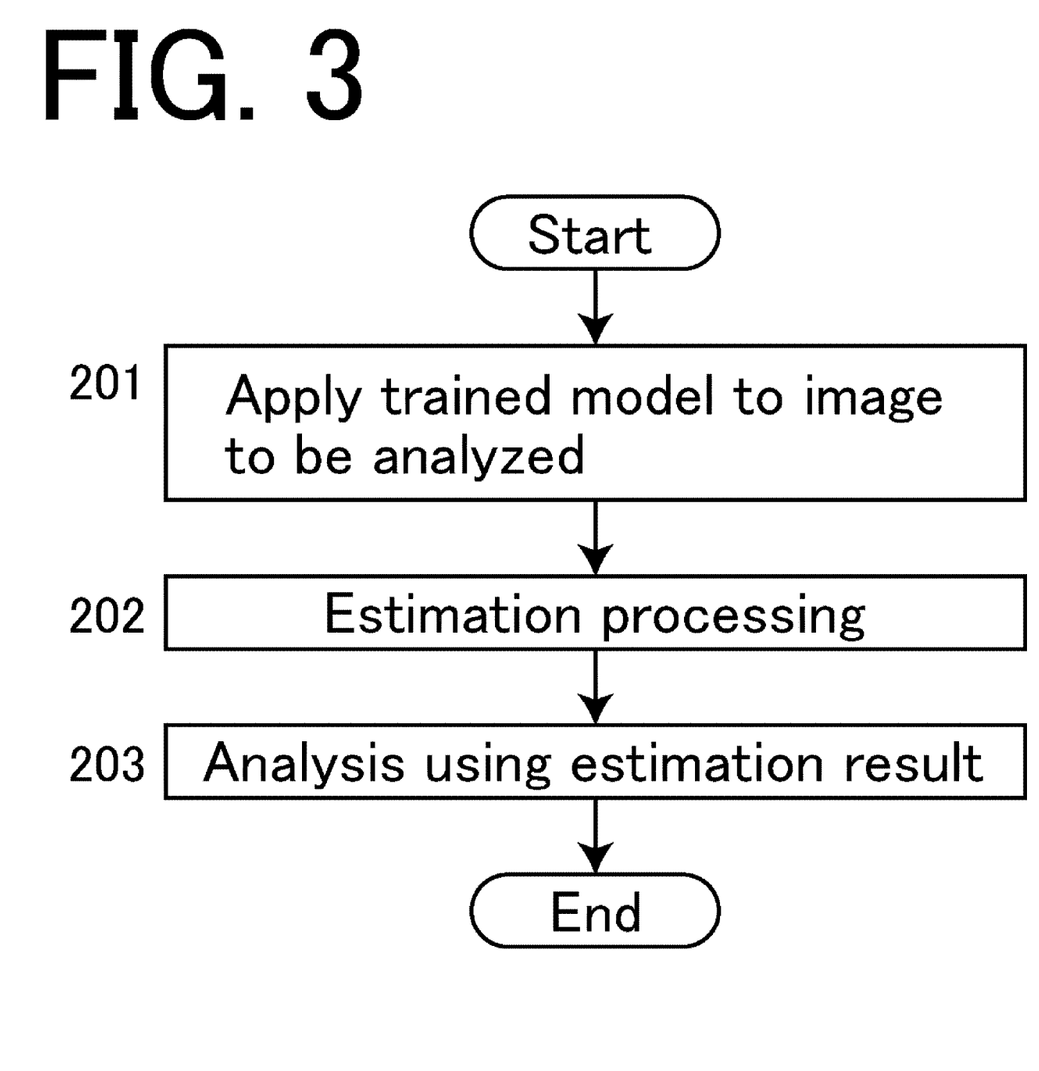
FIG. 3 is a flowchart illustrating an example of operation of the image analysis using a trained model.

FIG. 3 is an example of a process related to analysis using a trained model.

In the analysis processing using a trained model, the trained model is applied to an image to be analyzed (Step 201), and a boundary position of a cell region, a position of a cell nucleus, and the like in the image to be analyzed are estimated using each piece of parameter information of the trained model (Step 202). In subsequent analysis processing, the boundary position of a cell region, the position of a cell nucleus, and the like estimated by the estimation processing are used to count a total area of the cell region, cell nuclei, and the like (Step 203).

A series of operations related to creation of a trained model will be described with reference to FIGS. 5 to 7 together with a flowchart of FIG. 4.

Figure 5:
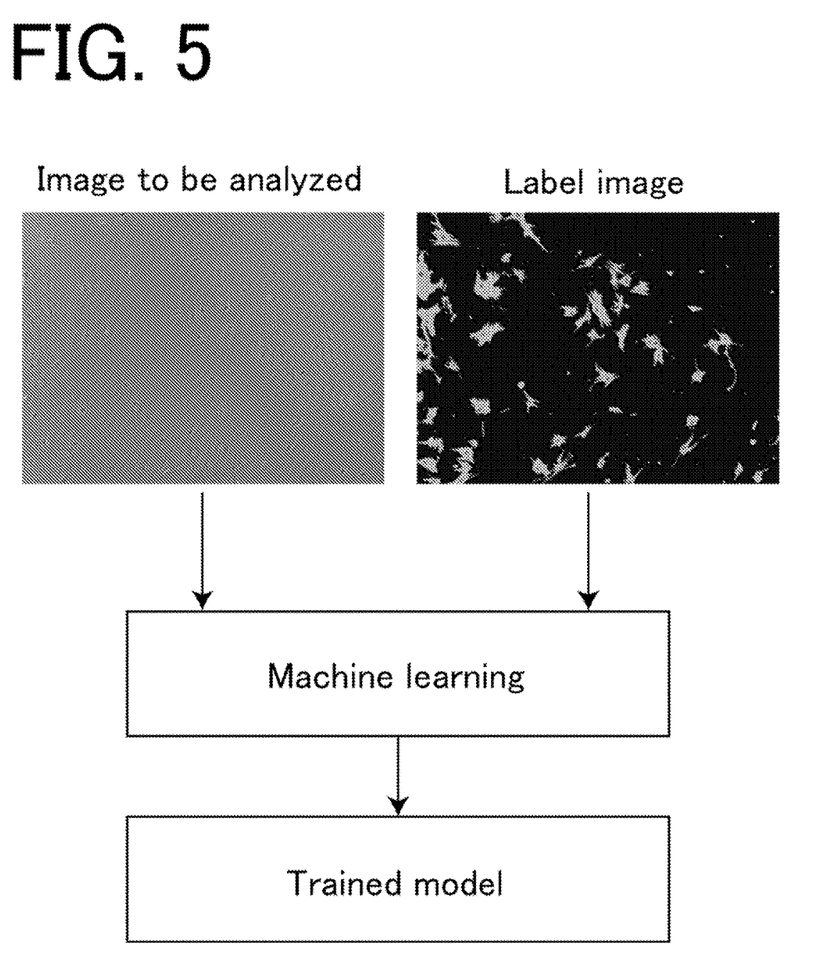
FIG. 5 is a flowchart illustrating an example of display of a list of data sets for training used for creating the trained model.
Figure 6:
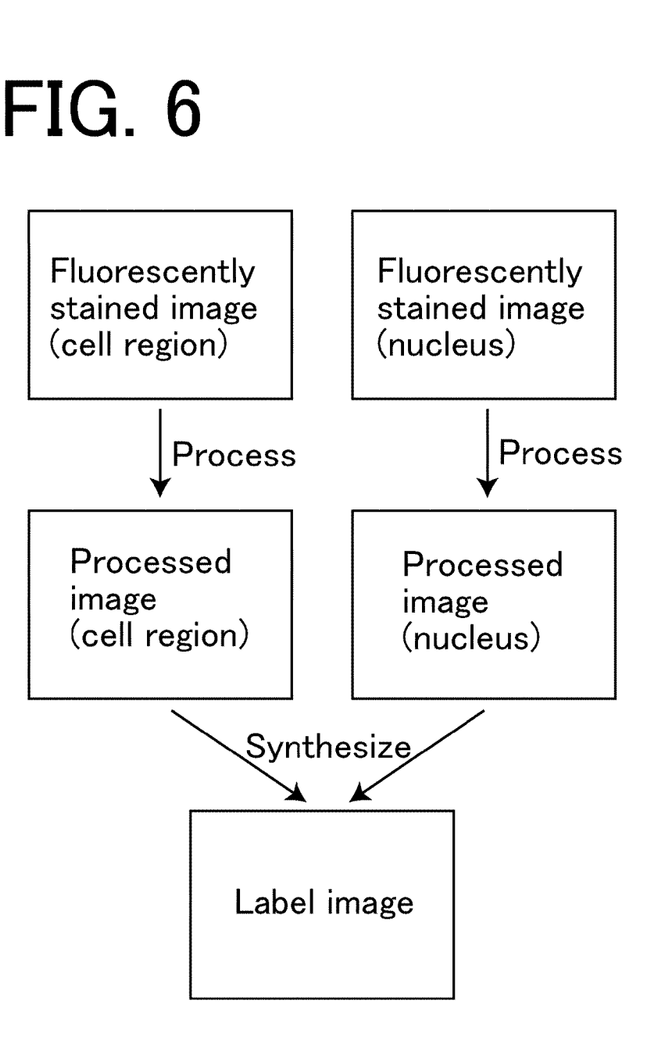
FIG. 6 is a conceptual diagram illustrating an example of a procedure of creating a label image.

In order to create a trained model, as illustrated in FIG. 5, an image to be analyzed and a label image corresponding to each image to be analyzed are required. As illustrated in FIG. 6, the label image can be acquired by applying processing such as binarization processing to each of fluorescently stained images obtained by fluorescently staining a cell and a nucleus in the same cell culture well as an image to be analyzed and imaging the cell and the nucleus with a fluorescence microscope to quantify a boundary portion of a portion to be analyzed in each image, and synthesizing the quantified processed images.

Here, a label image used for machine learning together with each image to be analyzed or an image on which a label image is based (for example, a fluorescently stained image) is defined as an "image for training". Then, a set of an image to be analyzed and a label image corresponding to the image to be analyzed or an image on which a label image is based is defined as a "data set for training".

Figure 4:
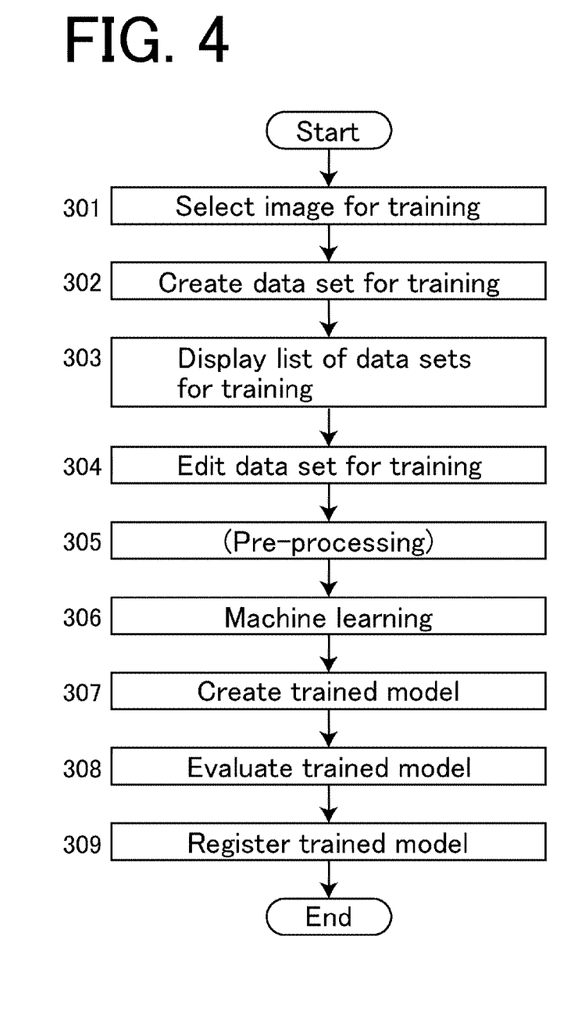
FIG. 4 is a flowchart illustrating an example of a series of operations related to creation of the trained model by machine learning.

Referring to the flowchart of FIG. 4, when creating an analysis recipe including machine learning, the recipe creation part 18 selects an image for training to be used for machine learning together with each image to be analyzed from among images held in the image holder 8 (Step 301). Since each image held in the image holder 8 is associated with information related to a culture condition of a cell shown in the image, it is possible to identify an image for training corresponding to each image to be analyzed by referring to the culture condition associated with each image. The recipe creation part 18 creates a data set for training by combining an image to be analyzed and an image for training under the same culture condition (well position or the like) (Step 302), and displays a list of images to be analyzed and images for training constituting each data set for training on the information display device 4 so that the images can be easily visually recognized (Step 303). The user can perform editing such as changing an image constituting each data set for training as necessary while checking the display of a list on the information display device 4 (Step 304). In a case where an image for training is an image on which a label image is based, the user can also select processing for converting the image into the label image.

Figure 7:
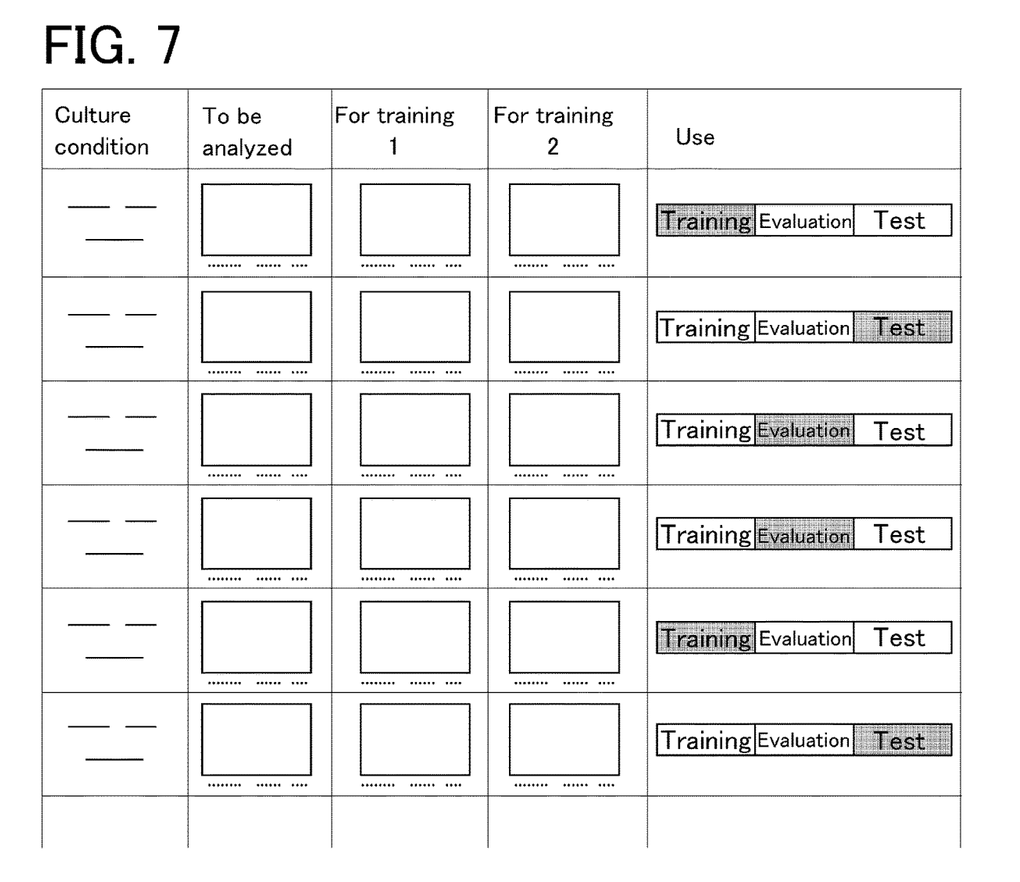
FIG. 7 is an example of display of a list of the data sets for training.

In an example of the display of a list of FIG. 7, data sets for training are displayed so as to be arranged in the vertical direction, and information related to a culture condition of each data set is displayed in the leftmost column. An image to be analyzed and an image for training constituting each data set are displayed side by side, and information such as a culture condition associated with each image is displayed below each image.

Furthermore, in this display of a list, items for setting the use of each data set for training are displayed, and each data set for training can be assigned to any of "Training", "Evaluation", and "Test". A data set for training assigned to "Training" is used to create a trained model by machine learning, and a data set for training assigned to "Evaluation" (also referred to as a data set for evaluation) is used to evaluate a created trained model. In a case where a plurality of data sets for training are assigned to "Training", a plurality of trained models are created, but each trained model is evaluated using a data set for evaluation, and only a trained model with highest evaluation is finally employed. A data set for training assigned to "Test" (also referred to as a data set for test) is used for testing a finally employed trained model.

Assignment of the use to each data set for training can be optionally performed by the user, but can also be automatically executed by the recipe creation part 18 in a case where the user desires. In a case where automatic assignment of the use to each data set for training is desired, the recipe creation part 18 classifies each data set for training into a plurality of sections depending on a difference in culture conditions, and assigns the use to each data set for training so that data sets for training assigned to each of "Training", "Evaluation", and "Test" substantially equally exist in each section.

As described above, when editing of a data set for training is completed (creation of a recipe is completed), the analysis execution part 20 performs pre-processing (for example, binarization processing of fluorescence detection image, and the like) of each image as necessary, then executes machine learning using each data set for training assigned to "Training" (Step 306), and creates a trained model (Step 307). After the above, evaluation using a data set for evaluation is performed for the created trained model (Step 308). The trained model registration part 10 registers a trained model having highest evaluation and causes the trained model holder 12 to hold the trained model (Step 309).

The example described above is merely an example of an embodiment of the image analyzing device according to the present invention, and the embodiment of the image analyzing device according to the present invention is as described below.

A first embodiment of the image analyzing device according to the present invention includes an image holder that holds an image, a trained model registration part configured to register trained models created by machine learning, a trained model holder that holds the trained models registered by the trained model registration part, an algorithm holder that holds a plurality of analysis algorithms for executing analysis processing of an image, a recipe creation part configured, for an image to be analyzed optionally selected from among images held in the image holder, to create an analysis recipe for analyzing the image to be analyzed by combining a trained model selected from the trained models held in the trained model holder and an analysis algorithm optionally selected from the plurality of analysis algorithms held in the algorithm holder, and an analysis execution part configured to execute analysis of the image to be analyzed based on the analysis recipe created by the recipe creation part.

In a first aspect of the first embodiment, the algorithm holder holds an analysis algorithm for creating a trained model by performing machine learning, the recipe creation part is configured to create an analysis recipe including machine learning for creating a trained model of the image to be analyzed in a case where the recipe creation part determines, based on information input by a user, that the trained model needs to be created, and is configured, when creating the analysis recipe including machine learning, to select an image for training to be used for the machine learning from among images held in the image holder and to create a data set for training including the image for training and the image to be analyzed, and the trained model registration part is configured to register a trained model created by the machine learning using the data set for training. According to such an aspect, a data set necessary for machine learning is automatically created by the user only preparing an image for training corresponding to an image to be analyzed, machine learning based on the data set is automatically executed, and a new trained model can be acquired.

As a first example in the first aspect, there is an example in which the image is an image obtained by imaging each of a plurality of cell culture wells provided in a cell culture plate, and each image is held in the image holder in a state of being associated with a culture condition of a cell in a cell culture well being imaged, and in a case where there are a plurality of the images to be analyzed and a plurality of the images for training when creating the analysis recipe including the machine learning, the recipe creation part is configured to create a plurality of the data sets for training by combining the image to be analyzed and the image for training corresponding to each other based on the culture condition associated with each image. In a case where there are a large number of images to be analyzed and images for training, work to create a data set for machine learning by associating the images to be analyzed with the images for training requires a lot of time, and there is a possibility of mistake in combining an image to be analyzed and an image for training. However, in the first example, since an image to be analyzed and an image for training are automatically combined according to a culture condition associated with each image to create a data set for training, a work load of the user when machine learning is executed is greatly reduced.

In the first example, the recipe creation part may be configured, when creating a plurality of the data sets for training, to present a list of the image to be analyzed and the image for training constituting each data set for training to the user together with a culture condition associated with each data set for training. According to such an aspect, the user can easily visually check details of each data set for training automatically created.

Further, in the first example, the recipe creation part may be configured, based on information input by a user, to set a part of a plurality of the data sets for training as a data set for evaluation for evaluating a created trained model. In such a case, the analysis execution part may be configured to create a trained model by performing the machine learning using the data set for training and to execute evaluation using the data set for evaluation for the created trained model, and the trained model registration part may be configured to register the trained model having a highest evaluation result. According to such an aspect, it is possible to acquire a trained model by which high analysis accuracy can be obtained for an image to be analyzed.

In the above case, the recipe creation part may be configured, when a user desires automatic selection of the data set for training to be the data set for evaluation, to classify a plurality of the data sets for training into a plurality of sections according to the culture condition and set at least one of the data sets for training belonging to each section as the data set for evaluation. According to such an aspect, a trained model applicable to a wide range of culture conditions can be acquired.

A second aspect in the first embodiment further includes an algorithm registration part configured to register a new analysis algorithm not held in the algorithm holder. The algorithm holder is configured to hold an analysis algorithm registered by the algorithm registration part. According to such an aspect, it is possible to increase the number of analysis algorithms that can be executed for an image to be analyzed.

A second embodiment of the image analyzing device according to the present invention includes an image holder that holds a plurality of images obtained by imaging each of a plurality of cell culture wells provided in a cell culture plate in a state of being associated with a culture condition of a cell in the imaged cell culture well, a recipe creation part configured to select a plurality of images for training corresponding to a plurality of images to be analyzed optionally selected from among images held in the image holder, to create a plurality of data sets for training by combining, based on the culture condition associated with each image, the image to be analyzed and the image for training corresponding to each other, and to create an analysis recipe for creating a trained model for image analysis by performing machine learning using the plurality of data sets for training, and an analysis execution part configured to create the trained model based on an analysis recipe created by the recipe creation part.

In a first aspect of the second embodiment, the recipe creation part is configured, when the plurality of data sets for training have been created, to present a list of the image to be analyzed and the image for training constituting each of the plurality of data sets for training to the user together with a culture condition associated with each of the plurality of data sets for training. According to such an aspect, the user can easily visually check details of each data set for training automatically created.

Further, in a second aspect of the second embodiment, the recipe creation part is configured to set a part of the plurality of data sets for training as a data set for evaluation for evaluating a created trained model based on information input by the user, and the analysis execution part is configured to create a trained model by performing the machine learning using the plurality of data sets for training and to execute evaluation using the data set for evaluation for the created trained model. According to such an aspect, evaluation of a trained model can be automatically executed.

In the second aspect, the recipe creation part may be configured, when a user desires automatic selection of the data set for training to be the data set for evaluation, to classify the plurality of data sets for training into a plurality of sections according to the culture condition and to set at least one of the data sets for training belonging to each section as the data set for evaluation. According to such an aspect, it is possible to evaluate whether or not a created trained model is applicable to a wide range of culture conditions.

DESCRIPTION OF REFERENCE SIGNS

1: Image analyzing device
2: Information processing device
4: Information display device 6: Image acquisition part
8: Image holder
10: Trained model registration part
12: Trained model holder
14: Algorithm holder
16: Algorithm registration part
18: Recipe creation part
20: Analysis execution part

The invention claimed is:

1. An image analyzing device comprising:
an image holder that holds an image;
a trained model registration part configured to register trained models created by machine learning;
a trained model holder that holds the trained models registered by the trained model registration part;
an algorithm holder that holds a plurality of analysis algorithms for executing analysis processing of an image;
a recipe creation part configured, for an image to be analyzed optionally selected from among images held in the image holder, to create an analysis recipe for analyzing the image to be analyzed by combining a trained model selected from the trained models held in the trained model holder and an analysis algorithm optionally selected from the plurality of analysis algorithms held in the algorithm holder; and
an analysis execution part configured to execute analysis of the image to be analyzed based on the analysis recipe created by the recipe creation part.

2. The image analyzing device according to claim 1, wherein
the algorithm holder holds an analysis algorithm for creating a trained model by performing machine learning,
the recipe creation part is configured to create an analysis recipe including machine learning for creating a trained model of the image to be analyzed in a case where the recipe creation part determines, based on information input by a user, that the trained model needs to be created, and is configured, when creating the analysis recipe including machine learning, to select an image for training to be used for the machine learning from among images held in the image holder and to create a data set for training including the image for training and the image to be analyzed, and
the trained model registration part is configured to register a trained model created by the machine learning using the data set for training.

3. The image analyzing device according to claim 2, wherein
the image is an image obtained by imaging each of a plurality of cell culture wells provided in a cell culture plate, and each image is held in the image holder in a state of being associated with a culture condition of a cell in a cell culture well being imaged, and
in a case where there are a plurality of the images to be analyzed and a plurality of the images for training when creating the analysis recipe including the machine learning, the recipe creation part is configured to create a plurality of the data sets for training by combining the image to be analyzed and the image for training corresponding to each other based on the culture condition associated with each image.

4. The image analyzing device according to claim 3, wherein the recipe creation part is configured, when creating a plurality of the data sets for training, to present a list of the image to be analyzed and the image for training constituting each data set for training to a user together with a culture condition associated with each data set for training.

5. The image analyzing device according to claim 3, wherein
the recipe creation part is configured, based on information input by a user, to set a part of a plurality of the data sets for training as a data set for evaluation for evaluating a created trained model,
the analysis execution part is configured to create a trained model by performing the machine learning using the data set for training and to execute evaluation using the data set for evaluation for the created trained model, and
the trained model registration part is configured to register the trained model having a highest evaluation result.

6. The image analyzing device according to claim 5, wherein the recipe creation part is configured, when a user desires automatic selection of the data set for training to be the data set for evaluation, to classify a plurality of the data sets for training into a plurality of sections according to the culture condition and to set at least one of the data sets for training belonging to each section as the data set for evaluation.

7. The image analyzing device according to claim 1, further comprising:
an algorithm registration part configured to register a new analysis algorithm not held in the algorithm holder, wherein
the algorithm holder is configured to hold an analysis algorithm registered by the algorithm registration part.

8. An image analyzing device comprising:
an image holder that holds a plurality of images obtained by imaging each of a plurality of cell culture wells provided in a cell culture plate in a state of being associated with a culture condition of a cell in the imaged cell culture well;
a recipe creation part configured to select a plurality of images for training corresponding to a plurality of images to be analyzed optionally selected from among images held in the image holder, to create a plurality of data sets for training by combining, based on the culture condition associated with each image, the image to be analyzed and the image for training corresponding to each other, and to create an analysis recipe for creating a trained model for image analysis by performing machine learning using the plurality of data sets for training; and
an analysis execution part configured to create the trained model based on an analysis recipe created by the recipe creation part.

9. The image analyzing device according to claim 8, wherein the recipe creation part is configured, when the plurality of data sets for training have been created, to present a list of the image to be analyzed and the image for training constituting each of the plurality of data sets for training to a user together with a culture condition associated with each of the plurality of data sets for training.

10. The image analyzing device according to claim 8, wherein
the recipe creation part is configured to set a part of the plurality of data sets for training as a data set for evaluation for evaluating a created trained model based on information input by a user, and
the analysis execution part is configured to create a trained model by performing the machine learning using the plurality of data sets for training and to execute evaluation using the data set for evaluation for the created trained model.

11. The image analyzing device according to claim 10, wherein the recipe creation part is configured, when a user desires automatic selection of the data set for training to be the data set for evaluation, to classify the plurality of data sets for training into a plurality of sections according to the culture condition and to set at least one of the data sets for training belonging to each section as the data set for evaluation.

* * * * *